(12) United States Patent
Huang et al.

(10) Patent No.: US 7,709,259 B2
(45) Date of Patent: May 4, 2010

(54) ENHANCEMENT OF MAMMALIAN EMBRYO DEVELOPMENT

(75) Inventors: Jaou-Chen Huang, Houston, TX (US); Jennifer S. Goldsby, Houston, TX (US); Wan-Song A. Wun, Houston, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 268 days.

(21) Appl. No.: 11/370,152

(22) Filed: Mar. 7, 2006

(65) Prior Publication Data

US 2006/0160213 A1    Jul. 20, 2006
US 2009/0011496 A9    Jan. 8, 2009

Related U.S. Application Data

(63) Continuation-in-part of application No. PCT/US2004/029167, filed on Sep. 8, 2004.

(60) Provisional application No. 60/708,291, filed on Aug. 15, 2005, provisional application No. 60/501,166, filed on Sep. 8, 2003.

(51) Int. Cl.
*C12N 5/00* (2006.01)
*C12N 5/02* (2006.01)

(52) U.S. Cl. ................. 435/387; 435/383; 435/404; 435/408; 435/366; 435/354

(58) Field of Classification Search ............ 435/387, 435/383, 404, 408, 366, 354
See application file for complete search history.

(56) References Cited

U.S. PATENT DOCUMENTS

| 5,096,822 A | 3/1992 | Rosenkrans, Jr. et al. |
| 6,100,249 A | 8/2000 | MacNamee |
| 2002/0088019 A1* | 7/2002 | Yacoby-Zeevi ............. 800/21 |

FOREIGN PATENT DOCUMENTS

WO          0032140 A1     6/2000

OTHER PUBLICATIONS

Chan. Prostaglandins. 42(4): 321-36, 1991.*
Garcia-Velasco et al. Curr. Op. in Obstetrics and Gynecology, 13: 299-304, 2001.*
Spinks et al. J. Of Reprod. Fertil., 88: 241-248, 1990.*
Battenfeld, R., et al., "Studies on Reproductive Toxicity of Iloprost in Rats, Rabbits, and Monkeys," Toxicology Letters 78 (Jan. 27, 1995), pp. 223-234.
Braude, P., et al., "Human Gene Expression First Occurs Between the Four- and Eight-Cell Stages of Preimplantation Development," Nature vol. 332 (Mar. 31, 1988) pp. 459-461.
Chida, S., et al., "Effects of Idomethacin, Prostaglandin E2, Prostaglandin F2 and 6-Keto-Prostaglandin F on Hatching of Mouse Blastocysts," Prostaglandins vol. 31, No. 2 (Feb. 1986) pp. 337-342.

Huang, J.C., et al., "Cycloxygenase-2-Derived Endogenous Prostacyclin Enhances Mouse Embryo Hatching," Human Reproduction vol. 19, No. 12 (Oct. 15, 2004) pp. 2900-2906.
Huang, J.C., et al., "Human Fallopian Tubes Express Prostacyclin (PGI) Synthase and Cyclooxygenases and Synthesize Abundant PGI," The Journal of Clinical Endocrinology & Metabolism 87(9) (Sep. 2002) pp. 4361-4368.
Huang, J.C., et al., "Oviduct Prostacyclin Functions as a Paracrine Factor to Augment the Development of Embryos," Human Reproduction vol. 19, No. 12 (Oct. 18, 2004) pp. 2907-2912.
Huang, J.C., et al., "Prostacyclin Enhances the Implantation and Live Birth Potentials of Mouse Embryos," Human Reproduction vol. 19, No. 8 (Jun. 17, 2004) pp. 1856-1860.
Huang, J.C., et al., "Prostacyclin Enhances Embryo Hatching But Not Sperm Motility," Human Reproduction vol. 18, No. 12, (2003), pp. 2582-2589.
Jones, M.A., et al., "Effects of Iloprost, a Stable Prostacyclin Analog, PGE2 and PGF2 on Rabbit Blastocysts," Gamete Research 20 (Jan. 20, 1988) pp. 203-213.
Lim, H., et al., "Cyclo-Oxygenase-2-Derived Prostacyclin Mediates Embryo Implantation in the Mouse Via PPAR," Genes & Development 13 (1999) pp. 1561-1574.
Lim, H., et al., "Multiple Female Reproductive Failures in Cyclooxygenase 2-Deficient Mice," Cell vol. 91 (Oct. 17, 1997) pp. 197-208.
Neulen, J., et al., "Arachidonic Acid Metabolism and Prostaglandin Production by Primate Preimplantation Blastocysts," Prostaglandins vol. 42, No. 2 (Aug. 1991) pp. 121-125.
O'Neill, C., et al., "Supplementation of In-Vitro Fertilisation Culture Medium with Platelet Activating Factor," The Lancet (Sep. 30, 1989) pp. 769-772.
Van Der Weiden, R.M.F., et al., "Prostanoid Levels in In Vitro Fertilization Culture Medium are Not Related to the Likelihood of Implantation," Fertility and Sterility vol. 62, No. 6 (Dec. 1994) pp. 1217-1220.
Xu, J.S., et al., "Temporal Effect of Human Oviductal Cell and its Derived Embryotrophic Factors on mouse Embryo Development," Biology of Reproduction 65 (Apr. 9, 2001) pp. 1481-1488.
Grunert, G.M., et al., "Prostacyclin Agonist (Iloprost) Enhances Human Embryo Development," Fertility & Sterility, vol. 48 (Supp./1)(2005) p. S237.
Supplementary Search Report issued on Jul. 4, 2008 by the European Patent Office for Application No. 04783425, 6 pages.

(Continued)

*Primary Examiner*—Thaian N Ton
(74) *Attorney, Agent, or Firm*—Conley Rose, P.C.

(57) ABSTRACT

A method of enhancing in vitro development of a mammalian embryo is disclosed which comprises supplementing the culture medium with a prostaglandin, or a prostaglandin analog, in an amount effective to promote complete hatching of the embryo (i.e., freeing of the embryo from the zona pellucida). The quality of human blastocysts is enhanced in vitro by culturing with a prostacyclin agonist, Iloprost. The in vivo implantation potential and live birth potential of an in vitro fertilization embryo is thereby enhanced and establishment of a viable pregnancy is facilitated.

21 Claims, 8 Drawing Sheets

OTHER PUBLICATIONS

Baskar J F et al: "Inhibition of Hatching of Mouse Blastocysts In-Vitro by Various Prostaglandin Antagonists" Journal of Reproduction and Fertility, Journals of Reproduction and Fertility Ltd, GB, vol. 63, No. 2, 1981, pp. 359-364, XP009097439 ISSN: 0022-4251.

Huang Jaou-Chen et al: "Enhanced hatching of mouse embryos by prostacyclin corresponded to the stage-specific expression of prostacyclin receptor by the mouse embryos." Fertility and Sterility, vol. 80, No. Suppl. 3, Sep. 2003, p. S21, XP009097607 & 59th Annual Meeting of the American Society for Reproductive Medicine; San Antonio, Texas, USA; Oct. 11-15, 2003 ISSN: 0015-0282.

Hurst P R et al: "Further Effects of Nonsteroidal Anti Inflammatory Compounds on Blastocyst Hatching In-Vitro and Implantation Rates in the Mouse" Biology of Reproduction, vol. 25, No. 4, 1981, pp. 777-784, XP002473568 ISSN: 0006-3363.

Piekos Marek W et al: "Evaluation of co-culture and alternative culture systems for promoting in-vitro development of mouse embryos" Human Reproduction (Oxford), vol. 10, No. 6, 1995, pp. 1486-1491, XP009097416 ISSN: 0268-1161.

Sayre B L et al: "Arachidonic acid metabolism during early development of ovine embryos: A possible relationship to shedding of the zona pellucida" Prostaglandins, vol. 45, No. 6, 1993, pp. 557-569, XP002474049 ISSN: 0090-6980.

Xu Jiasen et al: "Human oviductal cells reduce the incidence of apoptosis in cocultured mouse embryos" Fertility and Sterility, vol. 74, No. 6, Dec. 2000, pp. 1215-1219, XP002473142 ISSN: 0015-0282.

Examination Report for Indian Patent Application No. 1435/DELNP/2006, dated May 21, 2008, 4 pages.

Examination Report for Indian Patent Application No. 1435/DELNP/2006, dated Apr. 9, 2009, 3 pages.

Office Action for Chinese Patent Application No. 200480029052.6, dated May 9, 2008, 10 pages.

Response to Office Action for Chinese Patent Application No. 200480029052.6, dated Nov. 24, 2008, 7 pages (in Chinese).

International Search Report dated May 13, 2005 for International Application No. PCT/US04/29167, 2 pages.

International Preliminary Report on Patentability dated Mar. 13, 2006 for International Application No. PCT/US04/29167, 4 pages.

Communication pursuant to Article 9493) EPC dated Nov. 17, 2008 for European Patent Application No. 04783425.4, 6 pages.

Response to Communication pursuant to Article 9493) EPC dated May 26, 2009 for European Patent Application No. 04783425.4, 19 pages.

Response to Examination Report for Indian Patent Application No. 1435/DELNP/2006, dated Mar. 12, 2009, 3 pages.

Response to Examination Report for Indian Patent Application No. 1435/DELNP/2006, dated May 14, 2009, 3 pages.

* cited by examiner

Iloprost exposure based on stages of embryo development

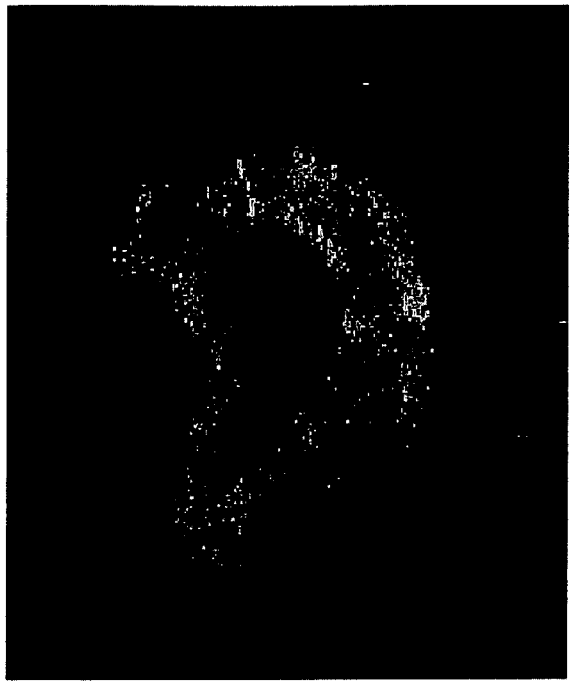
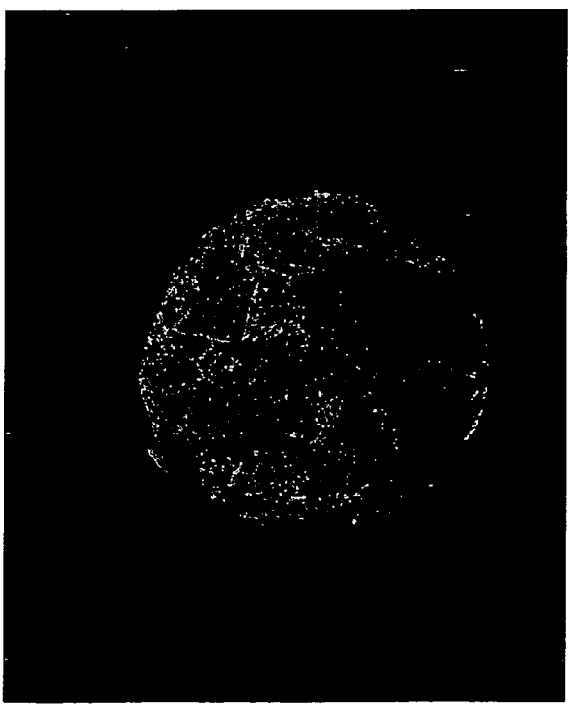
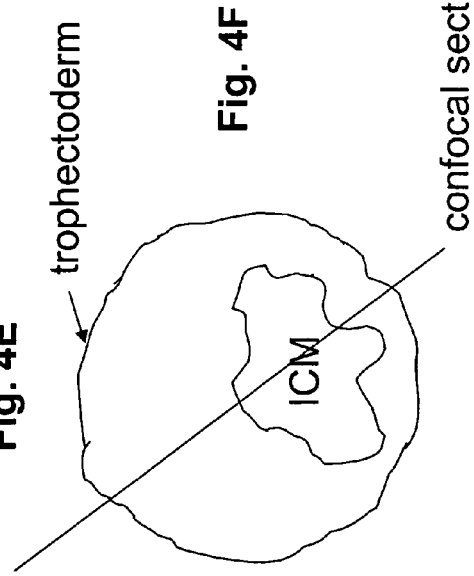
Fig. 4E
Fig. 4F
Fig. 4G

ENHANCEMENT OF MAMMALIAN EMBRYO DEVELOPMENT

CROSS-REFERENCE TO RELATED APPLICATIONS

This application is a continuation-in-part of PCT/US04/029167 filed Sep. 8, 2004, from which priority under 35 U.S.C. §120 is claimed. PCT/US04/029167 claims the benefit of U.S. Provisional Patent Application No. 60/501,166 filed Sep. 8, 2003. This application also claims the benefit under 35 U.S.C. §119(e) of U.S. Provisional Patent Application No. 60/708,291 filed Aug. 15, 2005. The disclosures of PCT/US04/029167 and 60/708,291 are hereby incorporated herein by reference.

STATEMENT REGARDING FEDERALLY SPONSORED RESEARCH OR DEVELOPMENT

This invention was made in part, with funding from the National Institute of Child Health and Human Development (NICHD), Contract No. HD01277. Accordingly, the United States Government has certain rights in this invention.

BACKGROUND OF THE INVENTION

1. Field of the Invention

The present invention generally relates to compositions and methods for in vitro culturing of mammalian embryos and for enhancing achievement of pregnancy after implantation of the cultured embryo in the uterus of a suitable mammalian host. More particularly, the invention pertains to such composition and methods which employ a prostaglandin or prostaglandin analog for enhancing blastocyst quality and improving implantation potential of a treated embryo.

2. Description of the Related Art

The environment within the oviduct enhances the fertilization potential of sperm and promotes the development of cleaving embryos. Embryos co-cultured with oviductal epithelial cells have been shown to have improved development, hatching and implantation [Xu, 2001; Xu, 2000]. Prostacyclin ($PGI_2$) is traditionally thought to be involved in maintaining blood and vascular homeostasis. However, recent observations in gene knock out mice suggest that it may have other physiological functions. The importance of endometrium-derived $PGI_2$ is underscored by the observations made in the cyclooxygenase (COX)-2 knockout mice [Lim, 1997]. The endometrium of the COX-2 knock out mice failed to decidualize normally. As a result, transferred wild type embryos could not implant in the female mice deficient in COX-2. The aforementioned abnormalities could be, to some extent, corrected by administration of an exogenous $PGI_2$ analog to the mother [Lim, 1999].

The role of oviduct-derived $PGI_2$ in the development of pre-implantation embryos is not clear, because the litter size of $PGI_2$ receptor (IP) knockout mice has not been compared with that of the wild type [Murata, 1997]. However, the genotypic distribution of pups arising from mating heterozygous IP knockout mice failed to conform to Mendel's Law: the prevalence of male and female pups with homozygous IP knockout genotype were 37% and 20%, respectively, less than expected [Murata, 1997].

SUMMARY OF PREFERRED EMBODIMENTS

It was recently discovered that the human oviduct synthesizes abundant prostacyclin ($PGI_2$) and $PGE_2$ [Huang, 2002]. Gene knockout studies suggest that endometrium-derived $PGI_2$ is essential to endometrial decidualization, but the effects of $PGI_2$ on the development of pre-implantation embryos have not been reported. Employing the hypothesis that optimal development of preimplantation embryos might require $PGI_2$, the effects of $PGI_2$ on mouse embryos were examined based on the rates of complete hatching. The expression of $PGI_2$ receptor (IP) was evaluated by Western blot analysis and immunohistochemistry. The binding of $PGI_2$ to embryos was confirmed by radioligand binding assay. Our results demonstrate that the hatching of mouse embryos is enhanced by supplementation of Iloprost ($ED_{50}$ 6.7 nM), a stable $PGI_2$ synthetic analog. Exposure to Iloprost during eight-cell to morulae or morulae to early blastocyst stages was critical to enhanced hatching. This stage-specific response to $PGI_2$ coincided with the developmental stage-specific expression of IP. Further studies were conducted in an attempt to correlate the enhanced embryo hatching with increased implantation and live births, mouse embryos cultured in media supplemented with Iloprost were transferred to gestational carriers. The number of gestation sacs and live pups was compared with that of control embryos. Because additives in culture media reportedly increased fetal weights [DeBaun, 2002; Thompson, 1995; Sinclair, 1999], the weights of the pups and the placentae were also compared. Our results indicate that culturing embryos in media supplemented with Iloprost enhances the implantation and live birth of mouse embryos without affecting the weights of the pups or the placentae.

Accordingly, in certain embodiments of the present invention, a method of enhancing in vitro development of an embryo comprising supplementing culture medium with a prostaglandin such as $PGI_2$ or $PGE_2$ or analog thereof is provided. In some embodiments, the prostaglandin is $PGI_2$ or $PGE_2$, and in some embodiments the prostaglandin analog is Iloprost or $PGE_1$. In some embodiments, the method includes adding the prostaglandin or analog to the culture medium in an amount sufficient to promote complete hatching of the embryo. Preferably "complete hatching" comprises freeing the embryo from the zona pellucida. In some embodiments of the method, supplementing of the culture medium is done during early developmental stage of the embryo during which time the genome is activated and the fertilized egg develops into morulae. In some embodiments in which the embryo is human, the early developmental stage commences with a four-to eight-cell state. In some embodiments of the method, supplementing of the culture medium is done during the morulae to early blastocyst stage development of the embryo. In some embodiments, supplementing of the culture medium is performed during both the early developmental stage to morulae stage development of the embryo and during the morulae to early blastocyst stage development of the embryo. In certain embodiments of the method, in which the embryo is of mouse origin, the supplementing step includes exposing the embryo in culture to the prostaglandin or analog between 24 to 42 hours after harvest of the embryo at its two-cell developmental stage. In certain embodiments of the method wherein the embryo is mouse, the step of supplementing during the morulae to early blastocyst stage comprises exposing the embryo to prostaglandin or prostaglandin analog at a time between 42 to 72 hours after harvest of the embryo at its two-cell developmental stage.

Also provided in accordance with certain embodiments of the present invention, is a method of increasing the in vivo implantation potential of an in vitro fertilization embryo. "Implantation potential" is the ability of the embryos to implant in the uterus. This method includes carrying out one of the above-described embodiments to enhance in vitro development of the embryo, such that complete hatching of the embryo in culture is achieved or hatching is enhanced, compared to other IVF methods. In accordance with certain embodiments of this method, the completely or nearly-hatched embryo is then introduced into the uterus of a mammalian host, such than enhanced implantation of the embryo is achieved. In some embodiments, complete hatching of the embryo in vitro correlates with establishment of a viable pregnancy.

In some embodiments of the present invention, a method of increasing the live birth potential of an in vitro fertilized mammalian embryo is provided. "Live birth potential" refers to the ability of an embryo to yield a live birth. The method comprises enhancing in vitro development of the embryo, as described above, by in vitro culturing with an amount of a prostaglandin or analog thereof, such that enhanced hatching potential or complete hatching of the embryos in culture is achieved. In preferred embodiments such treatment confers an enhanced potential for complete hatching even after the embryos are removed from culture and are in an in vivo environment. This property is referred to as "enhanced hatching potential." The hatched embryo, or the embryo with enhanced hatching potential, is then transferred to the uterus of a mammalian host; and the embryo is allowed to implant and grow in vivo, such that the ability of the embryo to yield a live birth is enhanced relative to that of an embryo that is implanted without enhancement of hatching.

In yet another embodiment of the present invention, a method of increasing the live birth rate in a group of in vitro fertilized mammalian embryos is provided which comprises enhancing in vitro development of the embryos according to an above-described method, such that enhancement of hatching, or, preferably, complete hatching of the embryos in culture is achieved. The method includes introducing or transferring the embryos into mammalian hosts; and then allowing the embryos to grow in vivo, wherein the rate of live births from the group of embryos with enhanced hatching is greater than the rate of live births from the group of embryos transferred into a host uterus without first being completely hatched or receiving enhancement of hatching.

Still further provided in accordance with certain embodiments of the invention is an improved cell culture medium for in vitro development of a mammalian embryo wherein the improvement includes a supplemental amount of a prostaglandin or analog thereof effective to enhance hatching, and, preferably, to promote complete hatching of the embryo in vitro. In some embodiments the medium contains an amount of prostaglandin, or analog thereof, that is effective to enhance complete hatching potential of the embryo after it has been removed from in vitro culture and transferred to the uterus of a mammalian host.

In accordance with certain embodiments, an in vitro method of enhancing the development of a mammalian embryo to at least the blastocyst stage is provided. The method includes obtaining an in vitro fertilization embryo comprising at least two cells; and growing the embryo in a culture medium supplemented with an amount of a prostaglandin or a prostaglandin analog effective for enhancing the quality of a resulting blastocyst. In some embodiments, enhancing blastocyst quality comprises blastocyst size. In some embodiments, enhancing blastocyst quality comprises increasing inner cell mass of the blastocyst. In some embodiments, enhancing blastocyst quality comprises increasing at least two qualities chosen from the group consisting of blastocyst size, inner cell mass and trophectoderm size. In some embodiments, the prostaglandin is prostacyclin ($PGI_2$) or prostaglandin $E_2$ ($PGE_2$). In some embodiments, the prostaglandin analog comprises a prostacyclin agonist (e.g., Iloprost). In some embodiments, the prostaglandin analog comprises prostaglandin $E_1$ ($PGE_1$).

Also provided in accordance with the present invention is a method of increasing the in vivo implantation potential of an in vitro fertilization embryo, which comprises culturing a mammalian zygote in vitro in a culture medium supplemented with an amount of a prostaglandin or a prostaglandin analog effective to promote an increase in quality of resulting blastocysts, whereby the in vivo implantation potential of a resulting embryo is enhanced. In some embodiments, culturing of a mammalian zygote in a culture medium supplemented with the prostaglandin or prostaglandin analog further enhances establishment of a viable pregnancy when the resulting embryo is implanted in a uterus. These and other embodiments, features and advantages of the present invention will become apparent with reference to the following description and drawings.

BRIEF DESCRIPTION OF THE DRAWINGS

FIGS. 4A-E and G are photomicrographs showing expression of prostacyclin receptor (IP) in morulae and blastocysts. Phase contrast (FIG. 4A) and IP staining (FIG. 4B) images of two morulae are shown. The zona pellucida is indicated by the arrow. FIG. 4C shows propidium iodide staining of nuclei in a blastocyst. In FIG. 4D the IP and propidium iodide staining of the blastocyst are superimposed. FIG. 4E shows IP staining of the blastocyst shows a reticular pattern. Clustered IP staining is seen only in the trophectoderm; the inner cell mass shows no increased staining. FIG. 4F is a sketch showing the location of the inner cell mass (ICM) within the blastocyst. FIG. 4G is the confocal microscopy image of a blastocyst showing that only the trophectoderm is stained by IP antibody. The plane of the section is indicated by the line in the panel F. There was no IP staining in negative controls, unfertilized oocytes or embryos at other developmental stages (not shown). The bar in the figure is approximately 20 μm.

FIG. 6A shows discrete blue bands (indicated by *) encircling the uterine horn that received embryos. In FIG. 6B, each blue band corresponded to a gestation sac, which appeared as pink-colored tissue in the opened uterine horn. No blue bands or gestation sacs were found in the uterine horn that did not receive embryos (marked by an arrow).

DETAILED DESCRIPTION OF PREFERRED EMBODIMENTS

Figure 1:
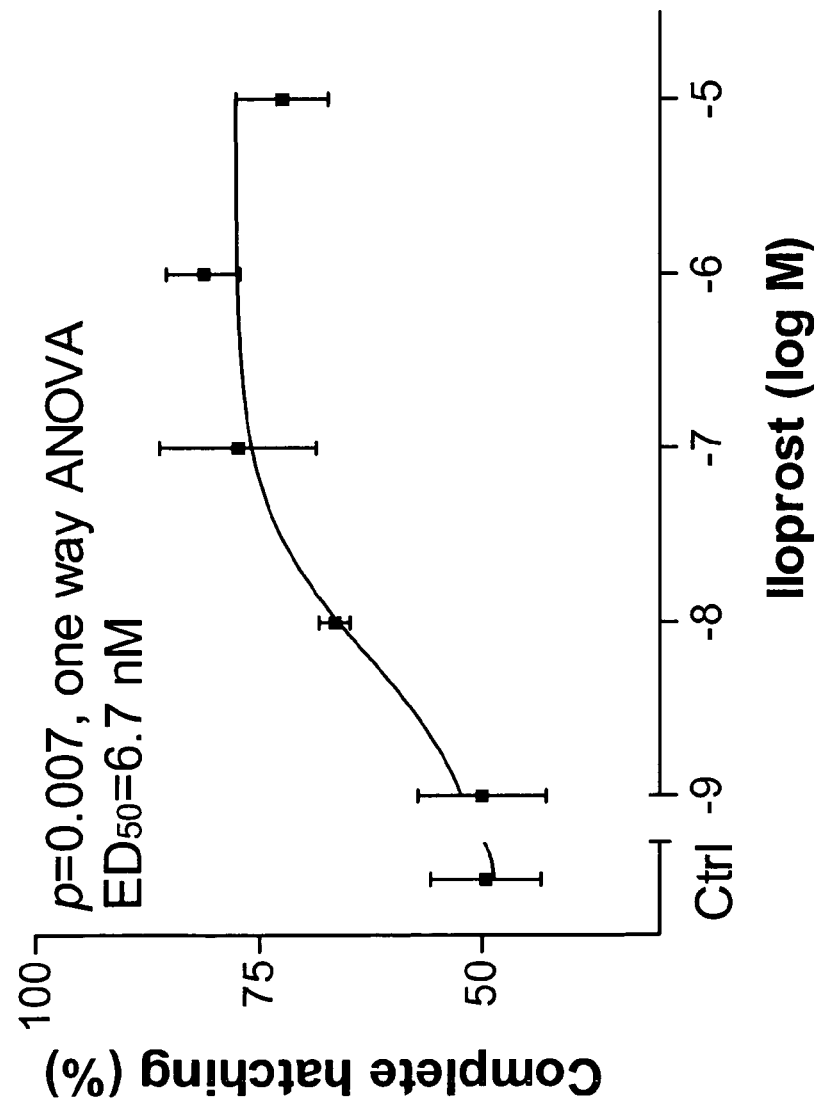
FIG. 1 is a graph showing prostacyclin ($PGI_2$) and complete hatching of mouse embryos. Two-cell mouse embryos were cultured with $PGI_2$ analog (Iloprost, 1 nM to 10 µM). The rate of complete hatching was determined 96 hours later. Results from three to five independent experiments (17-20 embryos each) are expressed as mean±S.D. The $ED_{50}$ value is approximately 6.7 nM.

The present disclosure developed in the course of investigating the effects of $PGI_2$ and $PGE_2$ on sperm and the embryo, and in subsequent investigations. Our recent results indicate that human [Huang, 2002] and mouse [Huang, 2004a] oviductal epithelial cells express enzymes essential to the synthesis of $PGI_2$, i.e. COX-1 or COX-2 and $PGI_2$ synthase. Abundant $PGI_2$ and $PGE_2$ was produced when $^{14}C$-arachidonic acid was incubated with microsomes prepared from human [Huang, 2002] or mouse oviduct [Huang, 2004a]. The present study also considered the fact that sperm travel to distal oviduct to fertilize the egg and the first 72 hours of embryo development takes place in the oviduct.

As part of the present study, the impact of $PGI_2$ on the embryos was evaluated by observing the complete hatching of mouse embryos cultured with $PGI_2$ analog. To further elucidate the mechanism, the expression of IP and the binding of embryos by radio-labeled Iloprost were also studied.

Materials and Methods

Source of Reagents and Institutional Approval

Unless stated otherwise, reagents were purchased from Sigma Co. (St. Louis, Mo., USA). The care of the laboratory animals and the research protocols were approved by the Animal Welfare Committee. Use of human samples was approved by the Committee for the Protection of Human Subjects (equivalent to an Institutional Review Board). These human embryo studies were carried out without funding from the United States Government.

Harvest and Culture of Mouse Embryos.

Mice were kept under controlled temperature, humidity, and light cycle (12 hour light/dark cycle) conditions with free access to water and food. Three-week old C57B1/6 female mice were purchased from Harlan (Indianapolis, Ind., USA). Eight-week old C3H male mice were purchased initially from Harlan and later from The Jackson Laboratory (Bar Harbor, Me., USA). Superovulation in the female mice was achieved by intraperitoneal injection of pregnant mare serum gonadotropin (5 IU), followed by human chorionic gonadotropin (hCG, 5 IU) 46 hours later. After receiving hCG, each female mouse was paired with one fertile male mouse. Forty-eight hours later, two-cell embryos were harvested from the oviduct into α-MEM media supplemented with 25 mM HEPES and 1% BSA (Irvine Scientific).

Embryos (17-20 per group) were cultured at 37° C. under 5% $CO_2$ in a four-well dish (Nalge Nunc International, Naperville, Ill., USA) containing 600 μl of medium in each well. The HTF and the α-MEM media were used sequentially during the 96-hour period to meet the changing nutritional requirements of the cleaving embryos [Gardner, 1998]. The HTF medium (SAGE Biopharma) was used during the first 48 hours, and the α-MEM medium (Irvine Scientific), with Earle's Salts and 2 mM glutamine, was used during the second 48 hours. The experimental embryos received Iloprost in water and the control embryos received an equal amount of water. Preliminary experiments showed that more than 95% of the embryos became blastocysts by 96 hours, similar to those cultured in KSOM media (Specialty Media, Cell and Molecular Technologies, Inc. Phillipsburg, N.J., USA). After 96-hour culture, each embryo was examined for the presence of the zona pellucida. Embryos completely free of the zona pellucida were counted as having completely hatched. The rate of complete hatching was determined by dividing the number of completely hatched embryos by the total number of embryos. Complete hatching of embryos was chosen as an endpoint instead of blastocyst formation or embryo hatching because the latter two markers are not correlated with establishment of a viable pregnancy [Lane, 1997].

Western Blot Analysis.

The deduced amino acid sequences of mouse IP (417 a.a., Genebank_BAA05144) and human IP (386 a.a., Genebank_BAA06110) are highly homologous [Katsuyama, 1994]. Preliminary studies confirmed that an affinity-purified polyclonal peptide antibody (a gift from Dr. Ke-He Ruan, University of Texas Health Science Center) cross-reacted with mouse IP. Western blot analysis was performed as described previously [Huang, 2002]. Briefly, total cell lysate from 60 mouse blastocysts was separated by electrophoresis on a 10% acrylamide gel (PAGE) and transferred to a nitrocellulose membrane (Schleicher & Schuell, Inc., Keene, N.H., USA). Immunoreactive protein was detected by incubation with the antibody and visualization with enhanced chemi-fluorescence (Amersham Biosciences, Piscataway, N.J., USA), detected using a STORM 860 laser scanner (Amersham Biosciences). Human platelet microsomes were used as positive controls. The antibody specificity was confirmed in parallel experiments using pre-absorbed antibody.

Immunohistochemistry, Fluorescence Microscopy and Confocal Microscopy.

Mouse embryos were fixed in 4% paraformaldehyde (pH 7.4) at 4° C. for 30 min. After three washes in PBS, the embryos were blocked for 20 min at room temperature in Tris-buffered saline (pH 7.4) containing 0.05% Tween-20, 5% powdered milk and 0.1% Triton X-100. The embryos were incubated with IP antibody (5 ng/ml) in blocking buffer for 2 hours then with goat anti-rabbit IgG coupled with Alexa 488 (2.5 μg/ml, Molecular Probes, Eugene, Oreg., USA) for 30 min at 37° C. Cell nuclei were counterstained with 10 μg/ml propidium iodide at room temperature for 20 min. The embryos were mounted in Fluoromount-G® (Southern Biotechnology Associates Inc., Birmingham, Ala., USA). For fluorescence microscopy, blastocysts were placed in the mounting media and overlaid with a coverslip. For confocal microscopy, a spacer of approximately 50 μm was placed between the slide and the coverslip to maintain the three dimensional morphology of the embryo. For negative controls, embryos were incubated with 10 ng/ml non-immune rabbit IgG (i.e., twice the concentration of primary antibody).

Fluorescence microscopy was performed using a Zeiss AxioPlan 2 microscope (Carl Zeiss, Baden-Wuerttemberg, Germany) equipped with appropriate filters. Images were captured using a CCD camera and processed by the AxioVision program (Version 3.0.6). Confocal microscopy was performed using a BioRad Radiance 2000 confocal system (Bio-Rad Laboratories, Hercules, Calif., USA) attached to an Olympus BX-50 microscope. The images were processed using the Image-Pro+ program (Media-Cybernetics, Carlsbad, Calif., USA).

Whole Embryo Radioligand Binding Assay.

Analysis of the binding of $^3$H-Iloprost to blastocysts was performed as previously described [Arbab, 2002] with slight modification. Two hundred thirty-two hatched and hatching blastocysts were washed three times in binding buffer (10 mM $MnCl_2$ in 10 mM HEPES, pH 7.4) and then transferred to 100 μl of binding buffer with or without unlabeled Iloprost (5 μM). The reaction was started by adding an equal amount of binding buffer containing $^3$H-Iloprost (200 nM, specific activity 11.0 Ci/mmol, Amersham Biosciences) and incubating for 60 min at room temperature. The reaction was terminated by transferring the blastocysts to 2 ml of ice-cold wash buffer (0.01% BSA in 10 mM HEPES, pH 7.4). The buffer and the blastocysts were filtered through glass fiber filters (Whatman GF/C 2.4 cm) and the filters were washed three times with 2 ml of wash buffer. The filters were dried in an oven before the radioactivity was determined by scintillation counting with 5 ml of scintillation fluid.

Statistical Analysis

Student's t-test or one-way analysis of variance followed by Dunnett test were used where appropriate. A $p<0.05$ was considered statistically significant. Construction of dose response curves and calculation of $ED_{50}$ values (with the Hill slope set at 1.0) were completed with the GraphPad Prism® software (GraphPad Prism Software Inc., San Diego, Calif., USA).

Embryo Transfer

Mouse embryos were harvested and cultured as described above, and subsequently published by the present inventor (Huang et al., 2003). Briefly, two-cell embryos (C3B6 μl) were harvested from super-ovulated, three-week old C57B1/6 female mice 42 hours after hCG injection. The embryos (14 per group) were cultured at 37° C. under 5% $CO_2$ in four-well dish (Nalge Nunc International, Naperville, Ill., USA) each containing 600 μl HTF media (SAGE Biopharma, Bedminster, N.J., USA). The experimental embryos received Iloprost (1 μM, Caymen Chemical, Ann Arbor, Mich., USA) in water and the control embryos, an equal amount of water. In either case, the volume of water was less than 0.1% of the culture media.

The day after the embryo donors received hCG, vaginal smears were obtained from potential gestational carriers (eight week old C3B6F1 female mice) to determine the stage of estrus cycle. Those in estrus were paired with vasectomized ICR males (Harlan) and checked for vaginal plugs on the following morning. Those with plugs were designated to be 0.5 day pseudopregnant.

Embryo transfer was performed on 2.5 day of pseudopregnancy under a dissecting microscope (Olympus SZ-PT). Surgical anesthesia was obtained through intraperitoneal injection of ketamine (200 mg/Kg) and xylazine (10 mg/Kg) (both from Burns Vet Supply Inc. TX, USA). Each uterine horn was accessed via a 2-cm flank incision. With the proximal oviduct held by a pair of forceps, an opening was created at the distal end of the uterine horn on the anti-mesenteric side with a 30 gauge needle. The opening permits the entry of transfer pipette which has an inner diameter of 135 μm (MidAtlantic Diagnostics, Inc. NJ, USA). Up to seven embryos in 0.8 μl of transfer media (α MEM with 25 mM HEPES and 1% BSA) were transferred to each horn. After each transfer, contents of the pipette were examined under a stereo microscope to identify retained embryos. The flank incision was closed with 9 mm metallic clips (Clay Adams, Parsippany, N.J., USA). To avoid mixing of control and experimental embryos due to embryo migration from one horn to the other (personal communication with Dr. Andreas Zimmer, University of Bonn, Germany), each gestational carrier received either control or experimental embryos. To maintain consistent transfer techniques, the embryo transfer was performed according to the same protocol and by one individual, who was blinded to the treatment the embryos being placed received. To ensure that both groups benefited equally from the experience gained over the course of the study (~6 months), the embryos were assigned treatments (control or Iloprost) in blocks of four.

Determination of Implantation Rate

Figure 6:
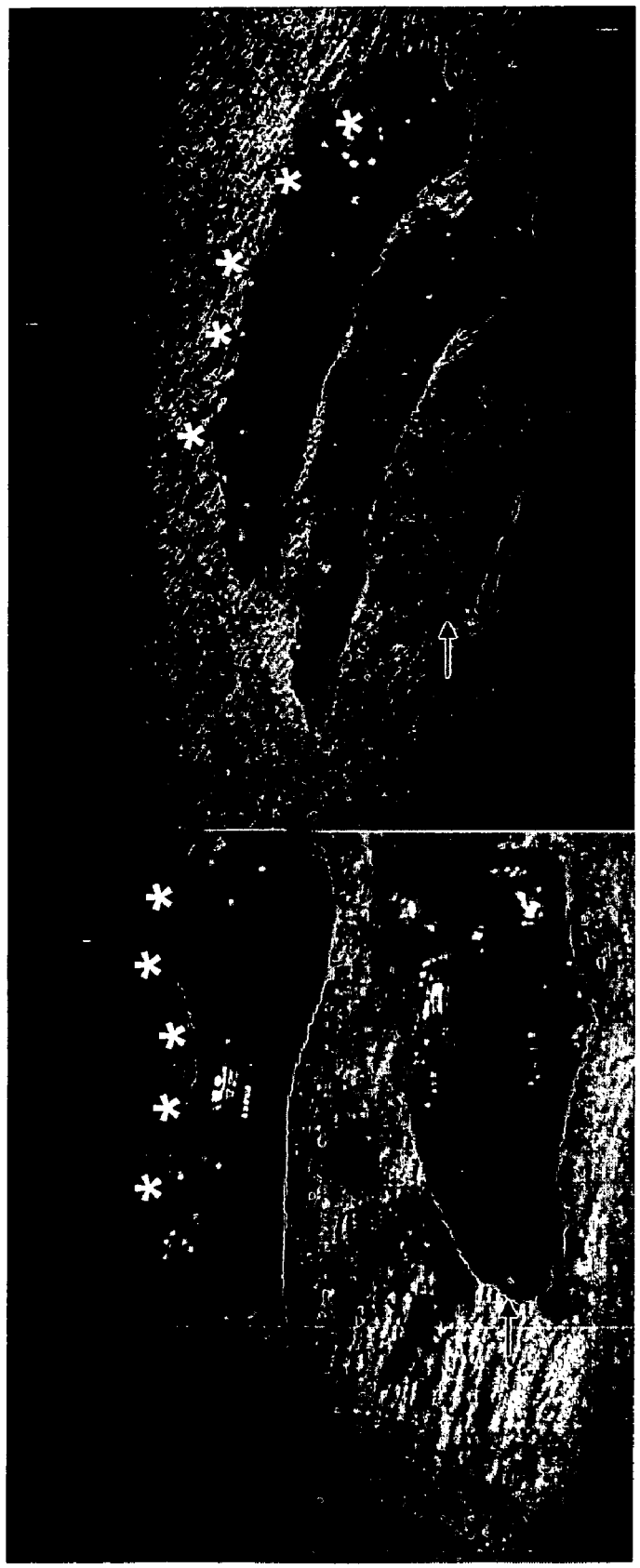
FIGS. 6A-B show gestation sacs in the uterus of gestational carriers. Implantation was determined by an increase in vascularity at the implantation site and confirmed by the presence of gestation sacs. Seventy two hours after embryo transfer, the gestational carrier was given 1% Chicago Blue via the tail vein and euthanized three minutes later.

Seventy-two hours after embryo transfer, implantation was determined based on a previously described method with some modifications (Paria et al., 1993). Briefly, three minutes before euthanasia, 0.1 ml Chicago Blue (1%) was injected via the tail vein of the gestational carrier. After the carrier was sacrificed, the uterine horns were removed. Discrete blue bands (indicated by *) encircling the uterine horns were counted (FIG. 6A). The presence of these bands reflect the increased vascular supply to the implantation sites. The uterine horns were then opened and the gestation sacs counted (FIG. 6B). The implantation rate was expressed as the number of gestation sacs per embryo transferred.

Determination of Live Birth Rate and the Weights of Pups and Placentae

Preliminary studies showed some gestational carriers cannibalize their pups when the litter size was small. In order to count and weigh the pups accurately, we sacrificed gestational carriers 14 days after embryo transfer (16.5 days of pregnancy or two days before natural birth). After euthanasia, the number of live pups was counted and the weight of individual pup and placenta was determined. All pups were examined for gross anomalies. The number of empty gestation sacs was also counted in order to determine the implantation rate. The live birth rate was expressed as the number of live pups per embryo transferred; the implantation rate was expressed as the number of sacs, with or without live pups, per embryo transferred.

Statistical Analysis

The Fisher's exact test was used to compare the rates; the Student's t-test was used to compare the weights. A $p<0.05$ was considered as statistically significant. The GraphPad Instat® software (GraphPad Software Inc., San Diego, Calif., USA) was used for statistical analysis.

Results $PGI_2$ Enhanced the Complete Hatching of Mouse Embryos

The complete hatching of mouse embryos was enhanced by Iloprost in a concentration-dependent manner. The effects were statistically significant at 0.1 μM or higher (FIG. 1). Maximum augmentation of complete embryo hatching occurred at 1 μM, where 81±7% (mean±S.D. n=3) of the experimental embryos hatched completely. In contrast, only 49±14% (mean±S.D. n=5) of the control embryos hatched completely. The $ED_{50}$ value derived from the dose response curve was 6.7 nM (FIG. 1). The saturable, concentration-dependent responses and the $ED_{50}$ value of 6.7 nM suggest that the effects of Iloprost were mediated by a receptor.

Duration of $PGI_2$ Exposure and the Developmental Stages of Embryos Critical to the Enhanced Hatching.

Figure 2:
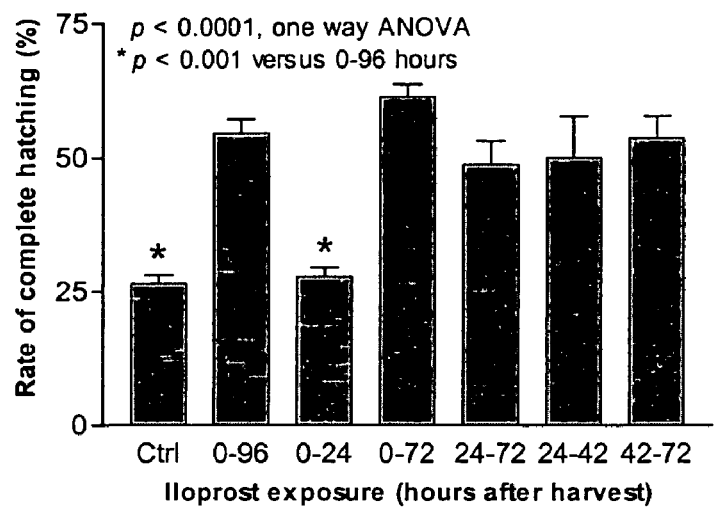
FIG. 2 is a bar graph showing augmentation of complete hatching and duration of prostacyclin ($PGI_2$) exposure (Iloprost exposure based on stages of embryo development). Two-cell mouse embryos were cultured in the presence of 0.1 µM Iloprost, a $PGI_2$ analog, during the indicated periods (expressed as hours after the harvest of two-cell embryos). The rate of complete hatching is expressed as mean±S.D. The developmental stages during which the embryos were exposed to Iloprost are listed in the table. Two periods appear critical to the full effects of Iloprost: 24-42 hours and 42-72 hours, corresponding to the development from eight-cell embryos to morulae and morulae to early blastocysts, respectively. Exposure to Iloprost during either period ensured enhanced hatching. The numbers of independent observations (each with 18-20 embryos) were: control, 12; 42-72 hours, 3; others, 4. The rate of complete hatching in the control embryos was different from that in FIG. 1, probably because the source of the male mice was changed.

Because embryos undergo several developmental stages before entering the uterus, we investigated developmental stage-specific responses to Iloprost. Our results indicate that some periods during the 96-hour culture were more critical than others. Exposure to Iloprost during the first 24 hours of culture (during this period most of the two-cell embryos developed into eight-cell embryos) did not enhance hatching (FIG. 2). On the other hand, exposure to Iloprost between 0-72 hours or 24-72 hours after harvest yielded the same rates of complete hatching as did 0-96 hours exposure (FIG. 2).

The two critical periods of exposure to Iloprost that ensured the full effects of Iloprost were between 24 to 42 hours and 42 to 72 hours after harvest, corresponding to the transformation from eight-cell embryos to morulae and from morulae to early blastocysts, respectively (table at bottom of FIG. 2). Our data indicate that brief exposure of embryos to $PGI_2$ confers an enhanced potential for complete hatching even after the embryos leave the oviduct.

Mouse Embryos Express IP.

Figure 3:
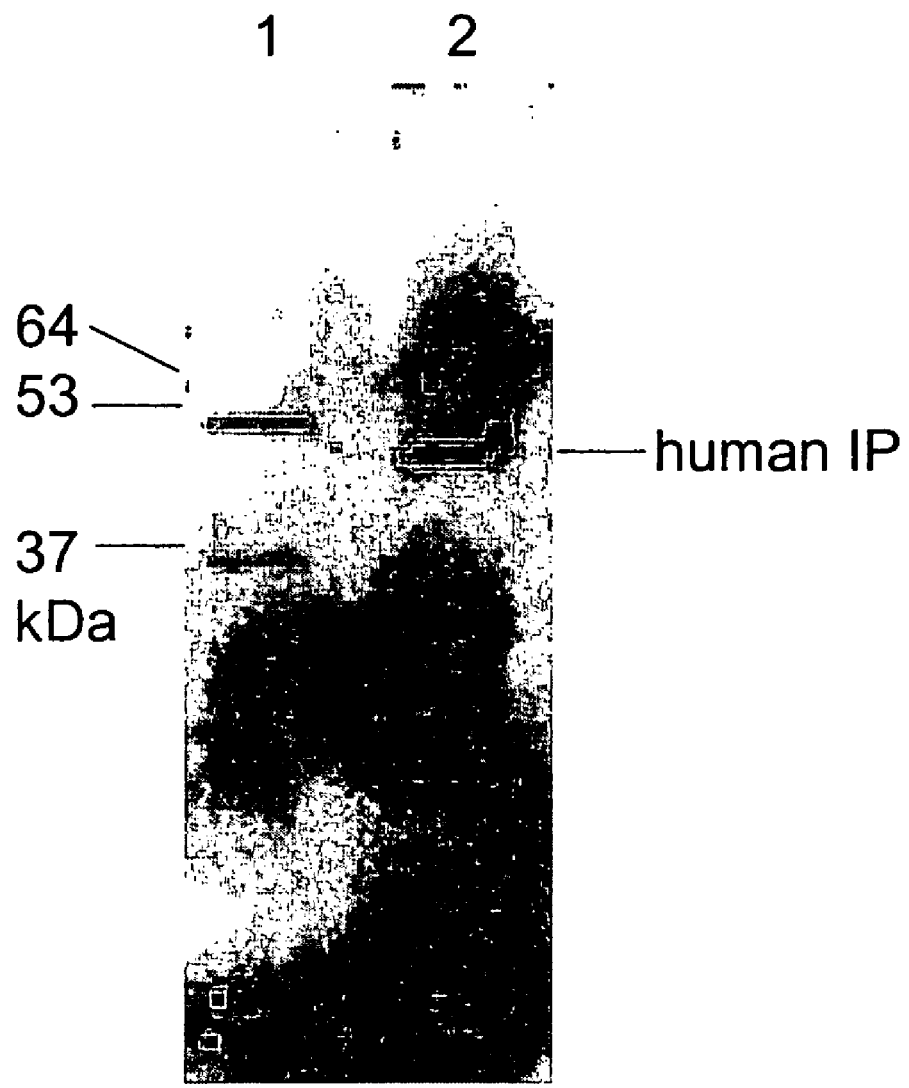
FIG. 3 is a Western blot showing expression of prostacyclin receptor (IP) in mouse embryos. Western blot analysis of total cell lysate from 60 mouse blastocysts (lane 1) and microsomes of human platelets (positive control, lane 2) showed immunoreaction with antibody against human IP. The migration of mouse IP was less than that of human IP, consistent with the expected molecular weights of ~50 kDa and ~46 kDa, respectively.
Figure 4A:
Figure 4B:
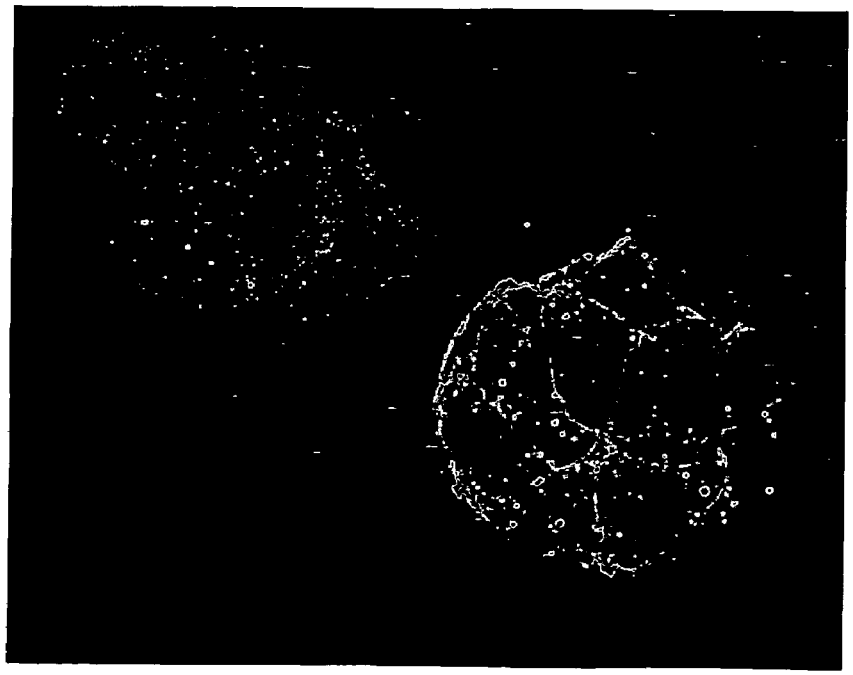
Figure 4C:
Figure 4D:
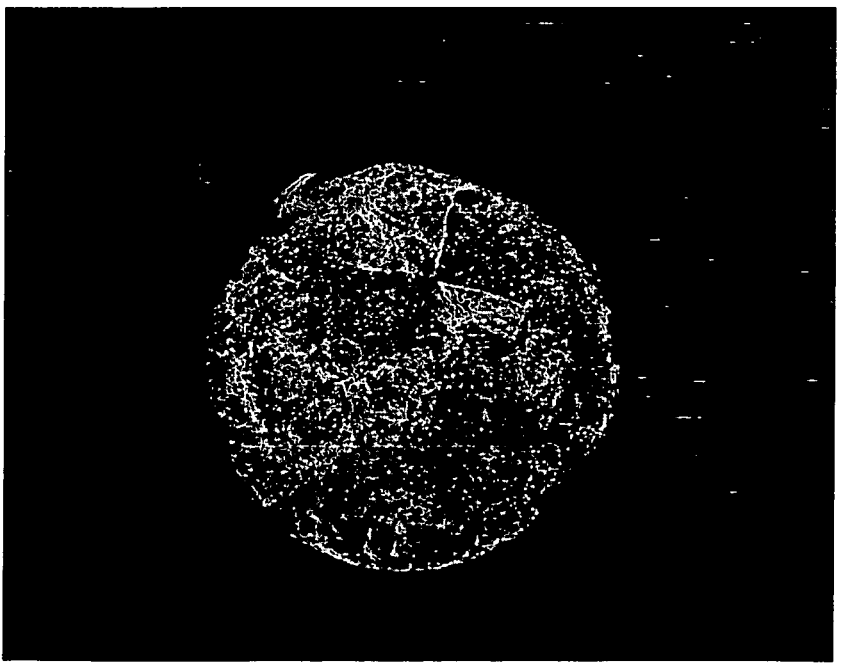

To investigate the developmental stage-specific expression of IP in mouse embryos, we performed Western blot analysis on blastocysts and immunohistochemistry on embryos at different developmental stages. Western blot analysis showed a protein of the expected molecular weight was detectable by the affinity-purified antibody against IP (FIG. 3). Fluorescence microscopy showed IP staining was present in morulae and blastocysts (FIG. 4A-E) but not in unfertilized egg, or in one-cell, two-cell, four-cell and eight-cell embryos (not shown). The IP staining in morulae and blastocysts shared the same fine, reticular pattern. Confocal microscopy images suggest that IP was preferentially expressed in the trophectoderm (FIG. 4G). Thus, the stage-specific expression of IP by the mouse embryo coincided with the responsiveness to Iloprost.

Radiolabeled Iloprost Binds to Mouse Embryo.

Figure 5:
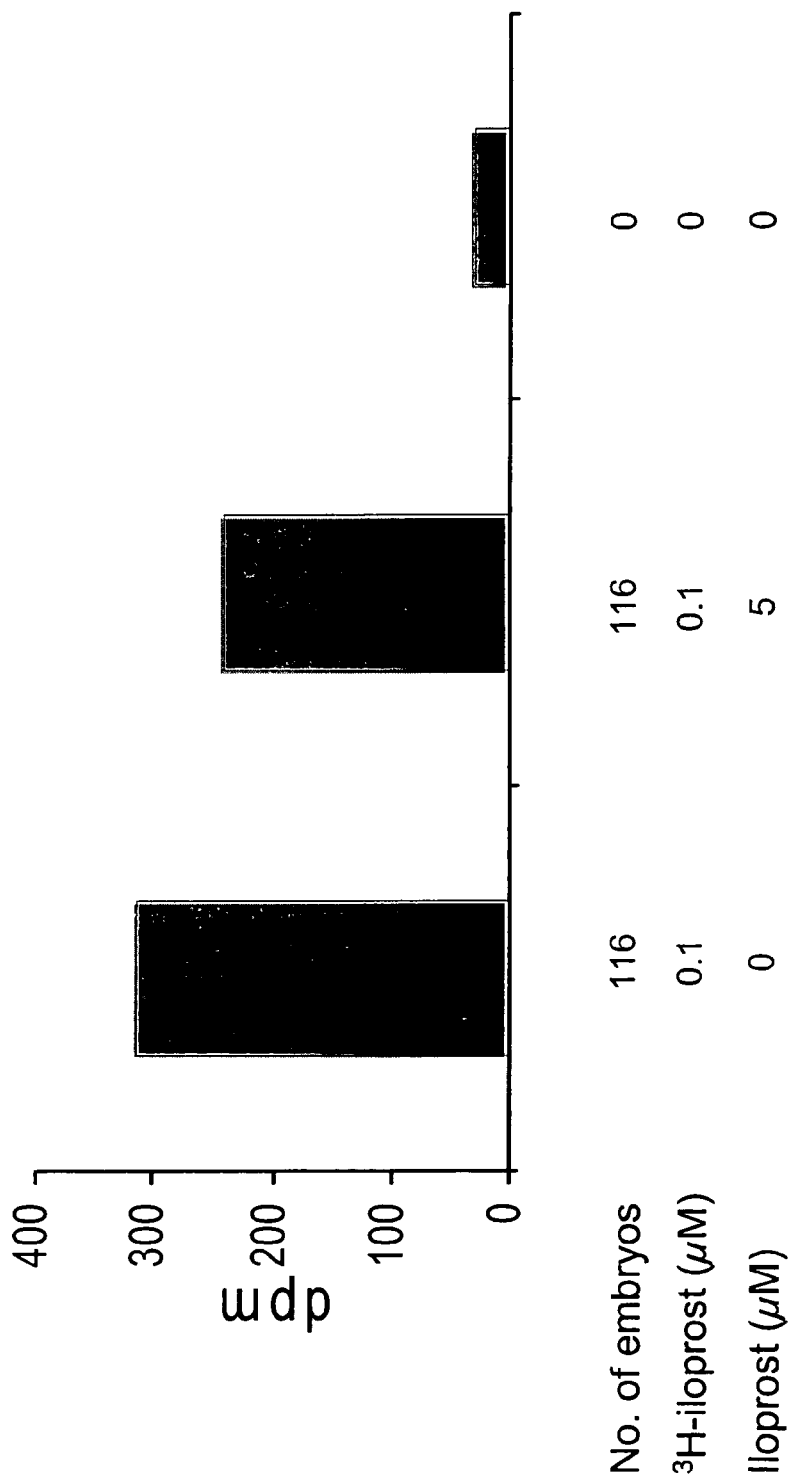
FIG. 5 is a bar graph showing Iloprost binding to intact mouse embryos. One hundred sixteen mouse blastocysts were incubated with 0.1 μM $^3$H-Iloprost, a $PGI_2$ analog, in the presence or absence of 5 μM unlabeled Iloprost. Bound and free $^3$H-Iloprost were separated by membrane filtration.

The concentration-dependent enhancement of complete embryo hatching by Iloprost suggested that the effect was receptor-mediated. We performed a radioligand binding assay to further confirm the binding of mouse embryos by Iloprost. We elected to quantitate Iloprost binding at a 0.1 µM level of the ligand, where augmented hatching was first observed and found that approximately 3.04 fmol $^3$H-Iloprost bound specifically to 116 blastocysts (FIG. 5).

Discussion

Our data indicate, for the first time, that $PGI_2$ enhances complete hatching of embryos. This concurs with previous reports that co-culture of mouse embryos with epithelial cells from human oviducts increased embryo cell number, reduced apoptosis, and improved embryo hatching [Piekos, 1995; Xu, 2000; Xu, 2001]. Thus, oviduct-derived $PGI_2$ and vascular endothelium-derived $PGI_2$ exert their effects in a similar, paracrine fashion. The former enhances embryo hatching; the latter prevents platelet aggregation. The concentration-dependent response was consistent with a receptor-mediated event and the $ED_{50}$ value of 6.7 nM was similar to the reported Kd value of solublized IP (8 nM) from human platelets [Tsai, 1989].

The response of embryos to Iloprost was developmental stage-specific and coincided with the expression of IP (FIG. 2). These critical periods for responsiveness coincided with the sojourn of mouse embryos in the oviduct, during which time the fertilized eggs develop into morulae. The relevant developmental stages also coincided with the activation of genome in human and mouse embryos, which takes place between the four- and eight-cell stages and after the two-cell stage, respectively [Tesarik, 1986; Tesarik, 1988; Braude, 1988].

Without wishing to be limited to a particular theory of how IP exerts its effects, it is proposed that embryos exposed to oviduct-derived $PGI_2$ or $PGE_2$ during early development retain the enhanced hatching potential when they reach the uterus. Through oviduct-derived $PGI_2$, the embryos, therefore, actively prepare themselves for implantation while they are in the oviduct. From the perspective of an embryo, oviduct-derived $PGI_2$ is complementary to endometrium-derived $PGI_2$, which mediates endometrial decidualization to ensure receptivity [Lim, 1999].

Without wishing to be limited to a particular theory, it is proposed that the enhanced hatching mediated by $PGI_2$ or $PGE_2$ may be due to an increased number of embryonic cells. Different mechanisms are involved in the hatching of mouse embryo in vitro and in vivo. Hatching in vitro involves blastocyst expansion, causing a global zonal thinning prior to zonal rupture, whereas hatching in vivo involves global zonal lysis by uterine or trophectodermal lysins [Montag, 2000]. Therefore, a sufficiently high number of embryonic cells is required to accomplish hatching in vitro. In this respect, our results are consistent with findings that embryos co-cultured with epithelial cells of the oviduct had more cells, less cell death, and improved hatching [Yeung, 1992; Xu, 2000]. In addition, $PGI_2$ may increase production of trypsin-like proteases by the trophectoderm to lyse the zona [Sawada, 1990; Perona, 1986].

The low implantation potential of IVF embryos (10-20% per embryo) [CDC, 2001] was attributed in part to sub-optimal culture conditions [De Vos, 2000]. Culture media have been modified to improve embryo development in vitro [Gardner, 1998]. Based on our data, supplementing media with $PGI_2$ and/or $PGE_2$ analog such as Iloprost, $PGE_1$ may provide an improved environment for the developing embryos and increase their implantation potential.

In conclusion, $PGI_2$ enhanced the complete hatching of cultured mouse embryos. The stage-specific expression of IP by the mouse embryos coincided with their responsiveness to $PGI_2$. Finally, based on our preliminary data, $PGE_2$ also enhanced the complete hatching of cultured mouse embryos.

In further studies we demonstrated that supplementing culture media with $PGI_2$ enhanced the implantation and potential live births of mouse embryos. These results corroborate and extend our initial observation that $PGI_2$ enhanced complete hatching of mouse embryos in culture [Huang, 2003]; they also support our hypothesis that oviduct-derived $PGI_2$ may serve a physiological function [Huang, 2002].

Table 1 shows that $PGI_2$ enhanced the implantation potentials of mouse embryos. Eighty-four control embryos and 81 Iloprost-treated embryos were transferred to 12 gestational carriers. Seventy two hours later, more gestation sacs were found in the Iloprost-treated group than the control group (76% versus 42%, relative risk 1.84, 95% confidence interval 1.38-2.43, p<0.0001). At the time of transfer, the developmental stages of the embryos were comparable.

Table 2 shows that $PGI_2$ Iloprost enhanced the live birth potentials of mouse embryos. Four hundred six control embryos and 415 Iloprost-treated embryos were transferred to 30 and 31 gestational carriers, respectively. The live birth rates of the control and the experimental groups were 28% and 36%, respectively (p=0.0017, relative risk 1.28, 95% confidence interval: 1.044-1.560). The weights of the pups and the placentae were comparable. Thus, $PGI_2$ increased the potential for live births of mouse embryos without affecting the weight of either the pups or the placentae. In addition, no gross anomalies were noted.

As noted above, approximately 70% of experimental and control embryos were at the morula stage at the time of transfer (Table 1), yet the transferred experimental embryos yielded more gestation sacs. These results validate our previous observation that exposure to $PGI_2$ between 8-cell and morula stages was sufficient to enhance the complete hatching of mouse embryos [Huang, 2003]. They are also consistent with oviduct-derived $PGI_2$ serving as an embryotrophic factor, because fertilized mouse eggs develop into morulae inside the oviduct [Snell, 1966].

The above-mentioned phenomenon indicates that $PGI_2$ initiates a chain of events culminating in enhanced hatching, implantation, and increased live births. In this regard, $PGI_2$ is reminiscent of platelet-activating factor (PAF) in which short term exposure to PAF increased the implantation of mouse [O'Neill, 1998] and human embryos [O'Neill, 1989]. The molecular and cellular events launched by $PGI_2$ must be critical to hatching. They may include increased embryonic cell number [Montag, 2000], augmented production of trypsin-like proteases by the trophectoderm [Sawada, 1990; Perona, 1986], enhanced blastocoele expansion due to enhanced $Na^+$-$K^+$-ATPase system of the trophectoderm [Biggers, 1988] or yet to be discovered mechanism(s).

The implantation rates of control embryos were comparable (42% and 46%) when examined 72 hours or 14 days after transfer, respectively. On the other hand, the implantation rate of experimental embryos examined 14 days after transfer (59%) was significantly less (p=0.038) than that examined 72 hours after transfer (76%). It is plausible that more sacs were completely resorbed in the experimental group due to crowding of implantation sites. Alternatively, Iloprost "rescued" some embryos that would otherwise not have implanted and only a fraction of those "rescued" embryos developed into live pups. Results from this study and abundant $PGI_2$ production by human [Huang, 2002] and mouse [Huang, 2004a] oviducts suggest that $PGI_2$ is one of the embryotrophic factors secreted by the oviducts, and thus supplementing embryo culture media with $PGI_2$ analog is expected to improve IVF outcome.

Supplementing IVF culture media with substances that enhance embryo development or implantation has been adopted by most laboratories and media manufacturers with great care. The concerns may include issues regarding reproductive toxicology, teratogenecity, and possibly, epigenetic effects of such manipulation. Lambs from ovine embryos cultured in media supplemented with human serum were heavier and had a longer gestation period [Thompson, 1995; Holm, 1996; Sinclair, 1999]. A congenital disorder involving overgrowth and neoplasia, the Beckwith-Wiedermann syndrome, was associated with assisted reproductive technology [DeBaun, 2002; Maher, 2003].

Reproductive toxicology studies on Iloprost [Battenfeld, 1995] showed embryonic and fetal development was not affected in rabbits and monkeys, but digit reduction was observed in rats. The digit anomaly is likely to be due to reduced uteroplacental flow causing hypoxia of the affected structure rather than the inherent teratogenicity of Iloprost, because Iloprost is a vasodilator and the studied animals received Iloprost throughout the gestation period. A similar defect could be induced by vasodilators with different chemical structures such as hydralazine and dihydropyridines. In the current study the exposure to Iloprost took place during the pre-implantation period. Among the 246 live pups examined, there was no digit reduction or other anomalies and the weights of pups and placentae between the two groups were similar. Despite all these, supplementing IVF media with $PGI_2$ analog should be considered an experimental protocol.

In these exemplary studies, we demonstrated that $PGI_2$ enhances the potentials of implantation and live births of mouse embryos without affecting the weights of either the fetuses or the placentae, i.e., prostacyclin did not increase the weights of the placenta or the baby. This is an advantage that is separate from the enhancement of implantation and live birth, and indicates that prostacyclin is different from other agents that enhance implantation and live birth. Previously reported agents which enhance implantation and live births also increase the weight of the babies, making those agents unsuitable for human in vitro fertilization (IVF) use. Moreover, because prostacyclin did not affect the weights of the placenta and the babies in the in vivo mouse model, it can be considered for use in human IVF embryos.

The results obtained in the foregoing in vivo studies of mouse embryos are considered representative or predictive of similar favorable in vivo results that will be obtained in other mammalian embryos, including human, when those embryos are similarly treated in vitro with prostaglandin or a prostaglandin analog prior to being transferred to the uterus. The current human IVF involves the transfer of 8-cell stage or blastocyst stage embryos to the patient's uterus. In this respect, the human IVF is similar to the design of our experiment involving transferring control or prostacyclin analog-treated embryos to gestational carriers. Our data showed, when transferred to gestational carriers, experimental embryos exposed to prostacyclin analog between 8-cell and morula stages had significantly higher rates of implantation and live births than control embryos (as shown in Tables 1 and 2, respectively).

Prostacyclin Agonist (Iloprost) Enhances Human Embryo Development.

In the above-described studies, and in WO 2005/026324 (The Board of Regents of the University of Texas System), the disclosure of which is hereby incorporated herein by reference, it is shown that supplementation of Iloprost significantly enhanced mouse embryo development to and beyond blastocyst stage [Huang et al. 2004b]. It was also disclosed that in Iloprost-treated mouse blastocysts transferred to gestational carriers, both the implantation rate and viable pulp rate were significantly increased [Huang et al. 2004c], with no significant difference in body weight between the control and experimental group [Huang et al. 2004c]. The inventors have carried out further studies of Iloprost treatment to enhance the development of human embryos. These human embryo studies were carried out without funding from the United States Government.

With the patients' written instructions, 101 frozen zygotes from 14 couples were used for the blastocyst formation study. The zygotes had been frozen during the period of January, 1993 to November, 2003. After overnight culture, only those embryos that had developed to 2-cell stage were used for further study. For each patient, those 2-cell stage embryos were split into a control pool or an experimental pool. All embryos were cultured in Gobal medium (a modified KSOM medium from IVF online) for 5 days with change medium at 2.5 day. The experimental group was supplemented with 0.1 µM of Iloprost (Cayman Chemical, Ann Arbor, Mich.). The control group was supplemented with vehicle (0.000001% DMSO). Chi-Square test were used to compare the number of blastocyst formed. The quality (size, inner cell mass, trophectoderm) of blastocysts was analyzed by non-parametric Wilcoxon Rank Sum Test. The statistical significance was defined at P<0.05. Another 52 donated frozen blastocysts, from 9 couples, were used for short term study. Forty-five thawed blastocysts were recovered. Those blastocysts were immediately cultured with or without Iloprost. The re-expansion of blastocoel was checked 18 hours later. The analysis of outcome was the same as the analysis for the frozen zygotes study. The results of this study are shown in Table 3.

Due to the limitation of human embryos available for research, the blastocyst formation rate was at border line (P=0.0506). As more zygotes become available for additional studies, it is expected that a significant increase in the blastocyst formation by Iloprost will be seen. We have reported that the size and quality of trophectoderm correlates with pregnancy [Wun et al. 2001a]. Low quality of inner cell mass correlates with spontaneous abortion [Wun et al. 2001b]. The significant enhancing of these three qualities observed in the present human studies suggests a possible increase in implantation and viable pregnancy rates by Iloprost treatment in human assisted reproductive technology (ART) cases. Although it initially appeared that Iloprost might help the thawed blastocysts, the trend was not significantly different. There are many possible mechanisms that may be responsible for the non-significant difference, such as the trauma from freezing and thawing, the duration of Iloprost treatment, the sensitivity of blastocyst to Iloprost, the required time to show morphological difference, or another mechanism.

In summary, this initial study using human embryos showed that Iloprost significantly enhances the quality of blastocysts. The enhancement of the three qualities: size, inner cell mass, and trophectoderm that was observed in the present human studies suggests a possible or probable increase in implantation and viable pregnancy rates by Iloprost treatment in human assisted reproductive technology (ART) cases. Further investigation is expected to clarify the mechanism of action of prostacyclin and its application to human ART.

TABLE 1

| | Treatment | | |
|---|---|---|---|
| | Control | Iloprost | p |
| Total embryos transferred | 84 | 81 | |
| Degenerated | 0 | 0 | n.s. |
| Morula | 48 | 49 | n.s. |
| Early Blastocyst+ | 12 | 8 | n.s. |

TABLE 1-continued

| | Treatment | | |
|---|---|---|---|
| | Control | Iloprost | p |
| Late Blastocyst+ | 24 | 22 | n.s. |
| Hatching Blastocyst | 0 | 2 | n.s. |
| Number of gestation sacs | 35 (42%) | 62 (76%) | <0.0001* | n.s. not significant

*Fisher's exact test, relative risk 1.84 (95% Confidence interval: 1.39-2.43)

+Early and late blastocysts denote embryos whose blastocoele cavity occupies <49% and ≥50% of the embryo, respectively.

TABLE 2

| | Treatment | | |
|---|---|---|---|
| | Control | Iloprost | p |
| Total embryos transferred | 406 | 415 | |
| Number of gestation carriers | 30 | 31 | |
| Total number of live pups | 115 (28%) | 149 (36%) | 0.017* |
| Pup weight (gm**) | 0.788 ± 0.151 | 0.772 ± 0.124 | n.s. |
| Placental weight (gm**) | 0.166 ± 0.037 | 0.166 ± 0.003 | n.s. | n.s. not significant

*Fisher's exact test, relative risk 1.28 (95% confidence interval: 1.04-1.56).

**expressed as mean ± S.D.

TABLE 3

| | Frozen Zygote | | | | Frozen blastocyst | | | |
|---|---|---|---|---|---|---|---|---|
| | Blastocyst formation rate | Size | ICM | TRO | Blastocyst formate rate | Size | ICM | TRO |
| Control | 42% (11/26) | 1.42 | 0.50 | 0.46 | 50% (11/22) | 1.45 | 0.72 | 0.68 |
| Iloprost | 69% (18/26) | 3.04 | 1.42 | 1.31 | 48% (11/23) | 1.47 | 0.86 | 0.78 |
| Statistical analysis | n.s. P = 0.0506 | P < 0.05 | P < 0.005 | P < 0.005 | n.s. | n.s. | n.s. | n.s. | n.s. not significant

The score of size is 1, 2, 3, 4, 5, 6. The coding for ICM and TRO is A = 3, B = 2, C = 1. For morula or degenerated embryos coding is 0.

REFERENCES

1. Arbab, F., Goldsby, J., Matijevic-Aleksic, N., Huang, G., Ruan, K. H., and Huang, J. C. (2002) Prostacyclin is an autocrine regulator in the contraction of oviductal smooth muscle. Hum Reprod. 17, 3053-9.
2. Battenfeld, R., Schuh, W., and Schobel, C. (1995) Studies on reproductive toxicity of iloprost in rats, rabbits and monkeys. Toxicol Lett. 78, 223-34.
3. Biggers, J. D., Bell, J. E., and Benos, D. J. (1988) Mammalian blastocyst: transport functions in a developing epithelium. Am J. Physiol. 255, C419-32.
4. Braude, P., Bolton, V., and Moore, S. (1988) Human gene expression first occurs between the four- and eight-cell stages of preimplantation development. Nature. 332, 459-61.

5. CDC. (2001). "ART Cycles Using Fresh, Nondonor Eggs or Embryos." 1999 Assisted Reproductive Technology Success Rates, National Summary and Fertility Clinic Reports, U.S. Department of Health and Human Services Center for Disease Control and Prevention, 35.
6. De Vos, A., and Van Steirteghem, A. (2000) Zona hardening, zona drilling and assisted hatching: new achievements in assisted reproduction. Cells Tissues Organs. 166, 220-7.
7. DeBaun, M. R., Niemitz, E. L., and Feinberg, A. P. (2002) Association of In Vitro Fertilization with Beckwith-Wiedemann Syndrome and Epigenetic Alterations of LIT1 and H19. Am J Hum Genet. 72, 1.
8. Gardner, D. K. (1998) Changes in requirements and utilization of nutrients during mammalian preimplantation embryo development and their significance in embryo culture. Theriogenology. 49, 83-102.
9. Holm, P., Walker, S. K., and Seamark, R. F. (1996) Embryo viability, duration of gestation and birth weight in sheep after transfer of in vitro matured and in vitro fertilized zygotes cultured in vitro or in vivo. J Reprod Fertil. 107, 175-81.
10. Huang, J. C., Arbab, F., Tumbusch, K. J., Goldsby, J. S., Matijevic-Aleksic, N., and Wu, K. K. (2002) Human Fallopian Tubes Express Prostacyclin (PGI) Synthase and Cyclooxygenases and Synthesize Abundant PGI. J Clin Endocrinol Metab. 87, 4361-4368.
11. Huang, J. C., Goldsby, J. S., Arbab, F., Melham, Z., Alecsic, N., and Wu, K. K. (2004a) Oviduct Prostacyclin Functions as a Paracrine Factor to Augment the Development of Embryos. Hum Reprod. 19:2907-12.
12. Huang, J.-C., Wun, W.-S. A., Goldsby, J. S., Wun, I. C., Falconi, S. M., and Wu, K. K. (2003) Prostacyclin enhances embryo hatching but not sperm motility. Hum. Reprod., 18, 2582-2589.
13. Katsuyama, M., Sugimoto, Y., Namba, T., Irie, A., Negishi, M., Narumiya, S., and Ichikawa, A. (1994) Cloning and expression of a cDNA for the human prostacyclin receptor. FEBS Lett. 344, 74-8.
14. Lane, M., and Gardner, D. K. (1997) Differential regulation of mouse embryo development and viability by amino acids. J Reprod Fertil. 109, 153-64.
15. Lim, H., Gupta, R. A., Ma, W. G., Paria, B. C., Moller, D. E., Morrow, J. D., DuBois, R. N., Trzaskos, J. M., and Dey, S. K. (1999) Cyclo-oxygenase-2-derived prostacyclin mediates embryo implantation in the mouse via PPAR-delta. Genes Dev. 13, 1561-74.
16. Lim, H., Paria, B. C., Das, S. K., Dinchuk, J. E., Langenbach, R., Trzaskos, J. M., and Dey, S. K. (1997) Multiple female reproductive failures in cyclooxygenase 2-deficient mice. Cell. 91, 197-208.
17. Maher, E. R., Brueton, L. A., Bowdin, S. C., Luharia, A., Cooper, W., Cole, T. R., Macdonald, F., Sampson, J. R., Barratt, C. L., Reik, W., and Hawkins, M. M. (2003) Beckwith-Wiedemann syndrome and assisted reproduction technology (ART). J Med Genet. 40, 62-64.
18. Montag, M., Koll, B., Holmes, P., and van der Ven, H. (2000) Significance of the number of embryonic cells and the state of the zona pellucida for hatching of mouse blastocysts in vitro versus in vivo. Biol Reprod. 62, 1738-44.
19. Murata, T., Ushikubi, F., Matsuoka, T., Hirata, M., Yamasaki, A., Sugimoto, Y., Ichikawa, A., Aze, Y., Tanaka, T., Yoshida, N., Ueno, A., Oh-ishi, S., and Narumiya, S. (1997) Altered pain perception and inflammatory response in mice lacking prostacyclin receptor. Nature. 388, 678-82.
20. O'Neill, C. (1998) Autocrine mediators are required to act on the embryo by the 2-cell stage to promote normal development and survival of mouse preimplantation embryos in vitro. Biol Reprod. 58, 1303-9.
21. O'Neill, C., Ryan, J. P., Collier, M., Saunders, D. M., Ammit, A. J., and Pike, I. L. (1989) Supplementation of in-vitro fertilisation culture medium with platelet activating factor. Lancet. 2, 769-72.
22. Paria, B. C., Huet-Hudson, Y. M., and Dey, S. K. (1993) Blastocyst's state of activity determines the "window" of implantation in the receptive mouse uterus. Proc Natl Acad Sci USA. 90, 10159-62.
23. Perona, R. M., and Wassarman, P. M. (1986) Mouse blastocysts hatch in vitro by using a trypsin-like proteinase associated with cells of mural trophectoderm. Dev Biol. 114, 42-52.
24. Piekos, M. W., Frasor, J., Mack, S., Binor, Z., Soltes, B., Molo, M. W., Radwanska, E., and Rawlins, R. G. (1995) Evaluation of co-culture and alternative culture systems for promoting in-vitro development of mouse embryos. Hum Reprod. 10, 1486-91.
25. Sawada, H., Yamazaki, K., and Hoshi, M. (1990) Trypsin-like hatching protease from mouse embryos: evidence for the presence in culture medium and its enzymatic properties. J Exp Zool. 254, 83-7.
26. Sinclair, K. D., McEvoy, T. G., Maxfield, E. K., Maltin, C. A., Young, L. E., Wilmut, I., Broadbent, P. J., and Robinson, J. J. (1999) Aberrant fetal growth and development after in vitro culture of sheep zygotes. J Reprod Fertil. 116, 177-86.
27. Snell, G. D., and Stevens, L. C. (1966). "Early embryology." Biology of the Laboratory Mouse by the staff of the Jackson Laboratory, E. L. Green, ed., Blakiston Division, McGraw-Hill Book Company, New York, 205-245.
28. Tesarik, J., Kopecny, V., Plachot, M., and Mandelbaum, J. (1986) Activation of nucleolar and extranucleolar RNA synthesis and changes in the ribosomal content of human embryos developing in vitro. J Reprod Fertil. 78, 463-70.
29. Tesarik, J., Kopecny, V., Plachot, M., and Mandelbaum, J. (1988) Early morphological signs of embryonic genome expression in human preimplantation development as revealed by quantitative electron microscopy. Dev Biol. 128, 15-20.
30. Thompson, J. G., Gardner, D. K., Pugh, P. A., McMillan, W. H., and Tervit, H. R. (1995) Lamb birth weight is affected by culture system utilized during in vitro pre-elongation development of ovine embryos. Biol Reprod. 53, 1385-91.
31. Tsai, A. L., Hsu, M. J., Vijjeswarapu, H., and Wu, K. K. (1989) Solubilization of prostacyclin membrane receptors from human platelets. J Biol. Chem. 264, 61-7.
32. Xu, J., Cheung, T. M., Chan, S. T., Ho, P. C., and Yeung, W. S. (2000) Human oviductal cells reduce the incidence of apoptosis in cocultured mouse embryos. Fertil Steril. 74, 1215-9.
33. Xu, J. S., Cheung, T. M., Chan, S. T., Ho, P. C., and Yeung, W. S. (2001) Temporal effect of human oviductal cell and its derived embryotrophic factors on mouse embryo development. Biol Reprod. 65, 1481-8.
34. Yeung, W. S., Ho, P. C., Lau, E. Y., and Chan, S. T. (1992) Improved development of human embryos in vitro by a human oviductal cell co-culture system. Hum Reprod. 7, 1144-9.
35. Huang, J.-C., Goldsby, J. S. and Wun, W.-S. A. (2004b) Prostayclin enhances the implantation and live birth potentials of mouse embryos. Hum Reprod 19:1856-1860.
36. Huang, J. C., Win, W. S., Goldsby, J. S., Matijevic-Aleksic, N., Wu, K. K. (2004c) Hum Reprod 19:2900-2906.

37. Wun, W. A., Grunert, G. M., Dunn, R. C., Valdes, C. T., Schenk, L. M., Mangal, R. K. (2001a) Fert. Steril. 76(Suppl. 1):S143-S144.

38. Wun, W-S. A., Grunert, G. M., Dunn, R., Valdes, C., Schenk, L., Mangal, R. (2001b) Fert. Steril. 78(Suppl. 1):S137-S138.

Without further elaboration, it is believed that one skilled in the art can, using the description herein, utilize the present invention to its fullest extent. The foregoing embodiments are to be construed as illustrative, and not as constraining the remainder of the disclosure in any way whatsoever. While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Any discussion of references in the Background of the Invention is not an admission that it is prior art to the present invention, especially any reference that may have a publication date after the priority date of this application. The disclosures of all patents, patent applications and publications cited herein are hereby incorporated herein by reference, to the extent that they provide exemplary, procedural or other details supplementary to those set forth herein.

What is claimed is:

1. A method of enhancing the blastocyst size, the inner cell mass or the trophectoderm size of a mouse or human blastocyst, comprising:
    obtaining an in vitro fertilization mouse or human pre-blastocyst embryo comprising at least two cells;
    growing said embryo in vitro to form a blastocyst in a culture medium supplemented with iloprost in an amount effective for enhancing at least one of blastocyst size, inner cell mass and trophectoderm size when compared to an untreated mouse or human embryo.

2. The method of claim 1 wherein said enhancing comprises increasing blastocyst size.

3. The method of claim 1 wherein said enhancing comprises increasing inner cell mass of said blastocyst.

4. The method of claim 1 wherein said enhancing comprises increasing trophectoderm size of said blastocyst.

5. The method of claim 1 wherein said enhancing comprises increasing at least two of blastocyst size, inner cell mass and trophectoderm size.

6. The method of claim 1, wherein said growing comprises forming a zona pellucida and wherein said amount of iloprost is also effective to enhance complete hatching of the blastocyst from said zona pellucida.

7. The method of claim 1, wherein said culture medium is supplemented with said iloprost during a first developmental stage of the embryo in which the genome is activated and the pre-blastocyst embryo develops into morulae.

8. The method of claim 7, wherein said embryo is human and the first developmental stage commences with a four- to eight-cell state.

9. The method of claim 7, wherein said culture medium is supplemented with said iloprost during a second developmental stage in which the morulae to early blastocyst stage development of the embryo occurs.

10. The method of claim 7, wherein said culture medium supplemented with said iloprost during both said first developmental stage in which the genome is activated and the pre-blastocyst embryo develops into morulae and during a second developmental state in which the morulae to early blastocyst stage development of the embryo occurs.

11. The method of claim 7, wherein said embryo is of mouse origin and said culture medium is supplemented with said iloprost between 24 to 42 hours after harvest of the embryo at its two-cell developmental stage.

12. The method of claim 7, wherein said embryo is mouse and the culture medium is supplemented with said iloprost between 42 to 72 hours after harvest of the embryo at its two-cell developmental stage.

13. The method of claim 1, wherein said amount of iloprost is in the range of about 0.001 to about 1.0 micromolar.

14. The method of claim 1, wherein said amount of iloprost is in the range of about 0.001 to about 0.1 micromolar.

15. The method of claim 1, wherein said amount of iloprost is about 6.7 nanomolar.

16. A method of increasing the in vivo implantation potential of an in vitro fertilization embryo, comprising:
    culturing a mouse or human zygote in vitro to form a blastocyst in a culture medium supplemented with iloprost in an amount effective to promote an increase in at least one of blastocyst size, inner cell mass and trophectoderm size, and enhance hatching of the blastocyst, whereby the in vivo implantation potential of a resulting embryo is enhanced, compared to a blastocyst formed from an untreated mouse or human zygote.

17. The method of claim 16, implanting the resulting embryo into a host uterus.

18. The method of claim 16, wherein said culturing further comprises forming a zona pellucida, and wherein said amount of iloprost is also effective to enhance complete hatching of said blastocyst from said zona pellucida.

19. The method of claim 16, wherein said amount of iloprost is in the range of about 0.001 to about 1.0 micromolar.

20. The method of claim 16, wherein said amount of iloprost is in the range of about 0.001 to about 0.1 micromolar.

21. The method of claim 16, wherein said amount of iloprost is about 6.7 nanomolar.

* * * * *